United States Patent [19]
Crowther et al.

[11] Patent Number: 6,025,512
[45] Date of Patent: Feb. 15, 2000

[54] PENTAFULVENE SYNTHESIS

[75] Inventors: Donna Jean Crowther; Jorge L. Zamora, both of Baytown, Tex.

[73] Assignee: Univation Technologies, LLC, Houston, Tex.

[21] Appl. No.: 09/226,404

[22] Filed: Jan. 6, 1999

[51] Int. Cl.[7] .............................. C07F 17/00; C07F 2/00
[52] U.S. Cl. ................ 556/43; 556/53; 585/317
[58] Field of Search .......................... 585/317; 556/43, 556/53

[56] References Cited

U.S. PATENT DOCUMENTS 5,840,948  11/1998  Rohrmann ................................. 556/11

OTHER PUBLICATIONS

*The Chemistry of Double–bonded Functional Groups,* edited by S. Patai, 1989, John Wiley and Sons Ltd., pp. 1133–1268.
J. Org. Chem., vol. 49, No. 11, pp. 1849–1853, 1984.
J. of Chem. Ed., vol. 63, No. 10, p. 916, 1986.
Pure and Applied Chem., vol. 58, No. 1, pp. 55–66, 1986.
Fulvenes and Sustituted Fulvenes, Ernst Bergman, received Apr. 12, 1967, pp. 41–84.
Tetrahedron Letters, vol. 34, No. 21, pp. 3445–3448, 1993.
J. Am. Chem. Soc., 105, pp. 928–932, 1983.
J. Chem. Research(s), p. 276, 1989.
J. Chem. Soc. (B), 1968, pp. 732–738.
Chemical Communications, 1970, pp. 935–936.
*Synthesis,* No. 9, Sep. 1970, pp. 449–465.
Chem. Ber. 121, pp. 207–218, 1988 (in German).
Chem., Ber. 119, pp. 1750–1754, 1986 (in German).
J. Org. Chem., vol. 59, No. 25, 1994, pp. 7723–7731.
Acc. Chem. Res., vol. 25, No. 10, 1992, pp. 461–467.
J. Org. Chem., vol. 52, No. 4, 1987, pp. 479–483.
J. Organometallic Chem. 96 (1975) pp. 399–433 (in German).
Liebigs Annalen der Chemie, Heft 1, Jan. 1988, pp. 39–42 (in German).
Organometallics, vol. 16, No. 13, 1997, pp. 2891–2899.
Bulletin of the Chemical Society of Japan, vol. 45, No. 10, Oct. 1972, pp. 3196–3201.
J. Chem. Soc. (C), vol. 11, 1969, pp. 1503–1504.
Helvetica Chimica Acta—vol. 53, Fasc. 6, 1970, Nr. 151–152 (in French).
Chem. Abstract accession No. 128:230518r (1988).
Tetrahedron Letters, vol. 23, No. 46, pp. 4773–4776, 1982.
Bull. Chem. Soc. Japan, 1995, 68(1), pp. 301–304.
J. Org. Chem., 1995, 60(4), pp. 813–820.

*Primary Examiner*—Porfirio Nazario-Gonzalez
*Attorney, Agent, or Firm*—Jaimes Sher; Catherine L. Bell; Lisa Kimes Jones

[57] ABSTRACT

This invention relates to a method to produce pentfulvenes comprising combining a partially substituted cyclopentadiene with a carbonyl containing compound and lithium or an alkyl lithium, wherein the partially substituted cyclopentadiene is represented by the formula:

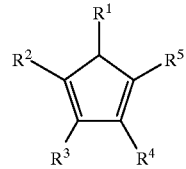

wherein the $R^1$ to $R^5$ groups are independently hydrogen or a $C_1$ to $C_{100}$ group, provided at least one R group is hydrogen but not more than three R groups are hydrogen.

15 Claims, No Drawings

PENTAFULVENE SYNTHESIS

FIELD OF THE INVENTION

This invention relates to a method to obtain pentafulvenes in high yield quickly and easily, and thus obtain cyclopentadienyl groups cleanly and in high yield.

BACKGROUND OF THE INVENTION

Cyclopentadienyl transition metal compounds are of particular interest in the polyolefin industry today for their use as polymerization catalysts. For example both biscyclopentadienyl and monocyclopentadienyl transition metal compounds (particularly of groups 4, 5 and 6) are known to polymerize olefins when used in combination with an activator such as an alumoxane or a non-coordinating anion. As interest in this area of chemistry has grown, so has the interest in substituting the cyclopentadienyl rings to tailor the catalysts to obtain different and hopefully unique products. Thus there is a need in the art for methods to quickly, easily and cleanly (i.e. get very high conversion without a significant number of side reactions or isomers) produce substituted cyclopentadienyl groups that can be used as ligands for catalyst production.

A common method to obtain substituted cyclopentadienyl compounds is to convert a substituted pentafulvene to a cyclopentadienyl group. Pentafulvenes are known to react with nucleophiles to produce substituted cyclopentadienides. (*The Chemistry of Double-bonded Functional Groups*, edited by S. Patai, 1989, John Wiley and Sons, pg 1133.) The difficult thing however, is to obtain pure cyclopentadiene structures that do not have to be "cleaned up" or otherwise treated. One way to accomplish this is by using pure pentafulvenes. Known pentafulvene syntheses, however, have generally suffered the drawbacks of producing side reactions, isomers and low yields.

Thus new means to obtain pentafulvenes in high yield and purity, quickly, easily and cleanly is desired in the art.

The most widely used pentafulvene synthesis was developed by Theile in 1900 and consists of condensation of cyclopentadiene with aldehydes or ketones in the presence of NaOEt, NaOH, or KOH in alcohol. The Theile synthesis is described as giving good yields for aliphatic and alicyclic ketones, medium yields for diaryl ketones or alkyl aryl ketones but in most cases low yields for aliphatic aldehydes. (ibib, pg 1149.) Once the aldehydes are more sterically shielded then better results are obtained. For example a 70% yield of 6-substituted pentafulvene (R1 was 2,5,5-trimethylpentene-1 and R2 was H) was obtained by combining a sterically shielded pr electronically stabilized aldehyde with Li cyclopentadienide in THF. (ibid, page 1151, cf R. D. Little, et al J. Am Chem. Soc. 105, 928, (1981).) Further work suggests that high yields of pentafulvenes can be obtained if the reaction is performed in an excess of pyrrolidine (in methanol). (ibid, pg1152) and J. Org. Chem. Vol 49, No. 11 1984 pg 1849–1853. Pyrrolidine however is expensive.

Hill, Jensen and Yaritz synthesized fulvenes from indenes and flourenes combined with an aldehyde or a ketone using a phase transfer catalyst (tetrabutylammonium hydrogen sulfate) and solid sodium hydroxide without resorting to a Grignard or alkali metal derivative. J. of Chem. Ed. Pg 916, 1986.

This invention address the need for clean, quick high yield methods to produce pentafulvenes.

SUMMARY OF THE INVENTION

This invention relates to a method to produce pentfulvenes comprising combining a partially substituted cyclopentadiene with lithium or an alkyl lithium and thereafter combining the partially substituted cyclopentadienide with a carbonyl containing compound, wherein the partially substituted cyclopentadiene is represented by the formula below including all the valence isomers:

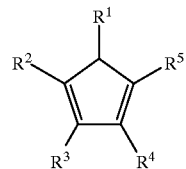

wherein the $R^1$ to $R^5$ are independently hydrogen or a $C_1$ to $C_{100}$ group, provided at least one R group is H but not more than three R groups are H.

DETAILED DESCRIPTION OF THE INVENTION

This invention relates to a method to produce pentfulvenes comprising combining a partially substituted cyclopentadiene with lithium or an alkyl lithium and thereafter combining the partially substituted cyclopentadienide with a carbonyl containing compound, wherein the partially substituted cyclopentadiene is represented by the formula including all its valence isomers:

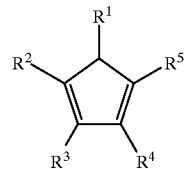

wherein the $R^1$ to $R^5$ are independently hydrogen or a $C_1$ to $C_{100}$ group, preferably a $C_1$ to $C_{10}$ group, even more preferably a $C_1$ to $C_6$ group, even more preferably a methyl, ethyl, propyl, butyl, phenyl or benzyl group, provided at least one R group is H but not more than three R groups are H. In a preferred embodiment $R^3$ and $R^4$ are not hydrogen. In another preferred embodiment three of the $R^1$ to $R^5$ groups are methyl groups, even more preferably four of the $R^1$ to $R^5$ groups are methyl groups. In a preferred embodiment one of the R groups is H and the rest are substituted. In another preferred embodiment one of the R groups is H and at least three of the other R groups are substituted. In another embodiment only two R groups are substituted and the reaction is performed at low temperatures, such as −80° C. to 10° C., preferably −80° C. to 0° C., more preferably −80° C. to −20° C.

The carbonyl containing compound is any compound containing a carbonyl group, preferably a $C_1$ to $C_{100}$ carbonyl containing compound, preferably a $C_1$ to $C_{20}$ carbonyl containing compound. In a preferred embodiment the carbonyl containing compound is represented by the formula:

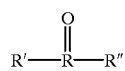

wherein R is a carbon, R' and R" are independently hydrogen, a linear, branched or cyclic $C_1$ to $C_{30}$ alkyl group or a heteroatom. In a preferred embodiment R" or R' contains a heteroatom. In a preferred embodiment R' and R"

are independently a linear, cyclic or branched $C_1$ to $C_{20}$ alkyl group. R' and R" may be joined so as to form a cyclic group such as a cyclohexanone. Preferred carbonyl containing compounds are aldehydes and ketones. Preferred aldehydes and ketones include acetone, benzophenone, methyl ethyl ketone, diethyl ketone, methyl isobutyl ketone, methyl isopropyl ketone, diisopropyl ketone, methyl tertiary butyl ketone, acetophenone, cyclohexanone, cyclopentanone, benzaldehyde, pivaldehyde, ethyl n-propyl ketone, ethyl isopropyl ketone, propionaldehyde, methyl ketone and the like.

The synthesis of the pentafulvene is typically performed by combining the partially substituted cyclopentadiene with lithium or an alkyl lithium compound typically in the presence of a solvent or diluent, (preferred alkyl groups for the alkyl lithium are linear, branched or cyclic $C_1$ to $C_{20}$ alkyls, such as methyl, propyl and butyl) then combining that reaction product with a carbonyl containing compound preferably in the presence of a solvent or a diluent. The reaction may be performed at any temperature, preferably at room temperature or below (such as between 25° C. and −80° C.), however if only two R groups are substituted the reaction is preferably performed at low temperatures, such as −80° C. to 10° C., preferably −80° C. to 0° C., more preferably −80° C. to −20° C. The solvent or diluent may be any solvent or diluent known in the art. Hydrocarbon solvents are suggested for use in this invention. Tetrahydrofuran is particularly suggested for use in this invention.

Preferred alkyl lithium compounds include n-butyl lithium, methyl lithium, propyl lithium, isobutyl lithium, hexyl lithium, pentyl lithium, septyl lithium, octyl lithium, 3,5,5-trimethylhexyl lithium, 3methylpentyl lithium, 4 methylpentyl lithium, cyclohexyl lithium and the like.

These pentafulvenes produced above may then be combined with a catalysts such as lithium aluminum hydride, alkyl lithium (alkyl is preferably a linear, branched or cyclic $C_1$ to $C_{20}$ alkyl), a Grinard reagent (MgBr), a sodium carbanion or potassium carbanion, preferably lithium or alkyl lithium to produce substituted cyclopentadienyl rings which may then be used to produce cyclopentadienyl transition metal catalysts that are then used to polymerize olefins. For example the substituted cyclopentadienyl rings may be reacted with a halogenated or alkylated transition metal compound to from a metallocene. Preferred transition metal compounds include halogenated or alkylated group 4 metals. Particularly preferred compounds include zirconium tetrachloride, hafnium tetrachloride, titanium tetrachloride and the like. In a preferred embodiment, the pentafulvene and the catalyst (such as a lithium aluminum hydride or an alkyl lithium) are allowed to react for about 16 hours or more, preferably about 18 hours or more, more preferably about 24 hours or more.

In a preferred embodiment a yield of 80% or more of the pentafulvene is obtained, preferably a yield of 90% or more, even more preferably of 95% or more. It is particularly beneficial that this invention is conducted in the absence of pyrrolidine.

EXAMPLES

Trimethylcyclopentadiene (90% 1,2,4-isomer) was received from Nippon Oil Co. Tetramethylcyclopentadiene was purchased from Boulder Scientific Co. Anhydrous THF was purchased from Aldrich and used without further purification.

Fulvene A

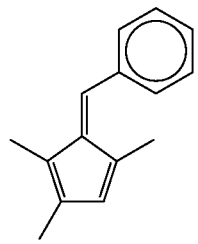

Benzaldehyde (3.00 g; 28 mmol) was dissolved in THF (150 ml) and reacted with lithium trimethylcyclopentadienide (3.28 g; 28 mmol) at room temperature. The reaction mixture was stirred overnight. Water was added to dissolve inorganic salts and the reaction mixture was extracted with $Et_2O$. After drying the $Et_2O$ layer with $MgSO_4$, all volatiles were removed to yield a dark brown oil (4.8 g; 87% yield). Analysis by $^1H$ NMR showed the oil to be at least 90% fulvene A.

Fulvene A (4.7g; 22 mmol) was then dissolved in $Et_2O$ and slowly reacted with solid $LiAlH_4$ (0.022g). The reaction was allowed to stir overnight. The product (Lithium 1,2,4-trimethyl, 3-benzylcyclopentadienide) was collected on a glass frit as a white solid (0.83 g).

Fulvene B

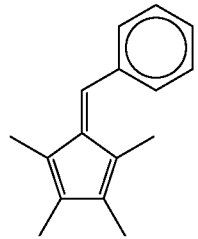

Benzaldehyde (3.000 g; 28 mmol) was dissolved in THF (150 ml) and reacted with lithium tetramethylcyclopentadienide at room temperature for 18 h. The reaction mixture was washed with water, extracted with $Et_2O$, and the ether layer dried with $MgSO_4$. After removing the $Et_2O$, the product was obtained as an oil (5.1 g; 86% yield). $^1H$ NMR showed the oil to be at least 90% Fulvene B.

Fulvene C

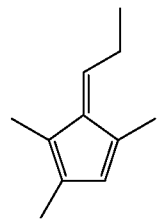

Lithium trimethycyclopentadienide (1.60 g; 14.0 mmol) was dissolved in 100 ml THF and cooled to −35° C. Propionaldehyde (0.81 g, 14.0 mmol) was added to the reaction mixture which was warmed at room temperature and allowed to react overnight.

$^1H$ NMR analysis showed fulvene C was present at at least 95% purity.

Fulvene C is fairly volatile at room temperature and yields are therefore somewhat lower when the compound is isolated as shown by the following example:

Lithium trimethycyclopentadienide (22.0 g; 191.3 mmol) was dissolved in 300 ml THF and cooled to 35° C. Propionaldehyde (11.0 g; 191.3 mmol) was added to the reaction mixture which was warmed to room temperature and allowed to react overnight. Water (100 ml) was added to dissolve inorganic salts and the reaction mixture was extracted with $Et_2O$. The $Et_2O$ layer was dried with $MgSO_4$ and reduced under a stream of nitrogen at room temperature to a bright orange oil (14.4 g; 51% yield).

Fulvene C (4.9 g; 33.1 mmol) was then dissolved in 100 ml $Et_2O$ and reacted with 1 equivalent of MeLi (1.4M in $Et_2O$) at room temperature. An oily material deposited on the reaction vessel walls. THF (40 ml) was added to dissolve the anion and the reaction mixture was poured into excess $Me_2SiCl_2$ (24 g). The volatiles were removed and the residue extracted with pentane. Removal of the pentane yielded a yellow oil (4.4 g; 50% yield) analyzed by $^1H$ NMR and shown to be 2,4,5-Trimethyl,3-secbutyl,1-dimethylchlorosilylcyclopentadiene.

All documents described herein are incorporated by reference herein, including any priority documents and/or testing procedures. As is apparent form the foregoing general description and the specific embodiments, while forms of the invention have been illustrated and described, various modifications can be made without departing from the spirit and scope of the invention. Accordingly it is not intended that the invention be limited thereby.

We claim:

1. A method to produce pentafulvenes comprising combining a partially substituted cyclopentadiene with lithium or an alkyl lithium and thereafter combining the partially substituted cyclopentadiene with a carbonyl containing compound, and reacting the pentafulvene with lithium aluminum hydride, alkyl lithium, a Grinard reagent, a sodium ion, or potassium ion to form a product, wherein the partially substituted cyclopentadienide is represented by the formula including all the valence isomers:

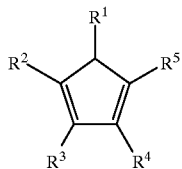

wherein the $R^1$ to $R^5$ groups are independently hydrogen or a $C_1$ to $C_{100}$ group, provided at least one R group is hydrogen but not more than three R groups are hydrogen.

2. The method of claim 1 wherein four of the R groups are a $C_1$ to $C_{10}$ group.

3. The method of claim 1 wherein four of the R groups are a $C_1$ to $C_6$ group.

4. The method of claim 1 wherein four of the R groups are a methyl, ethyl, propyl, butyl, phenyl or benzyl group.

5. The method of claim 1 wherein three R groups are a $C_1$ to $C_{100}$ group.

6. The method of claim 1 wherein four of the R groups are a $C_1$ to $C_{100}$ group.

7. The method of claim 1 wherein four of R groups are a methyl, ethyl, propyl, butyl, phenyl or benzyl group.

8. The method of claim 1 wherein $R^3$ and $R^4$ are not hydrogen.

9. The method of claim 1 wherein three of the R groups are methyl groups.

10. The method of claim 1 wherein four of the R groups are methyl groups.

11. The method of claim 1 wherein the reaction is performed at between 25° C. and −80° C.

12. The method of claim 1 wherein the reaction is performed in hydrocarbon solvent.

13. The method of claim 1 wherein the pentafulvene is reacted with lithium aluminum hydride or an alkyl lithium.

14. The method of claim 1 further comprising reacting the product with a halogenated or alkylated transition metal compound.

15. The method of claim 1 wherein the pentafulvene and the lithium aluminum hydride, the alkyl lithium, the Grinard reagent, the sodium ion or the potassium anion are allowed to react for at least 16 hours.

* * * * *